(12) United States Patent
Haisch et al.

(10) Patent No.: US 7,445,448 B2
(45) Date of Patent: Nov. 4, 2008

(54) METHOD FOR IDENTIFYING TOOTH-COLORED TOOTH FILLING RESIDUES

(75) Inventors: Michael Haisch, Aalen (DE); Ludwin Monz, Mainz (DE)

(73) Assignee: Carl Zeiss AG (DE)

( * ) Notice: Subject to any disclaimer, the term of this patent is extended or adjusted under 35 U.S.C. 154(b) by 314 days.

(21) Appl. No.: 10/892,019

(22) Filed: Jul. 15, 2004

(65) Prior Publication Data

US 2005/0014106 A1    Jan. 20, 2005

(30) Foreign Application Priority Data

Jul. 17, 2003    (DE)    ............... 103 33 515

(51) Int. Cl.
*A61C 5/00*    (2006.01)
*A61C 1/00*    (2006.01)

(52) U.S. Cl. .................................. 433/215; 433/29

(58) Field of Classification Search ............... 433/29, 433/215
See application file for complete search history.

(56) References Cited

U.S. PATENT DOCUMENTS

| | | | |
|---|---|---|---|
| 4,564,355 A * | 1/1986 | Traiger et al. ............... 433/215 |
| 5,211,748 A * | 5/1993 | Robinson et al. .............. 106/35 |
| 5,306,144 A | 4/1994 | Hibst et al. .................... 433/29 |
| 5,476,379 A * | 12/1995 | Disel ........................... 433/29 |
| 5,759,032 A * | 6/1998 | Bartel ........................... 433/29 |
| 6,171,105 B1 * | 1/2001 | Sarmadi ....................... 433/29 |
| 6,208,788 B1 * | 3/2001 | Nosov ......................... 385/121 |
| 6,413,084 B1 * | 7/2002 | Rubbert et al. .................. 433/29 |
| 6,769,911 B2 * | 8/2004 | Buchalla et al. ............... 433/29 |
| 2001/0023057 A1 * | 9/2001 | Alexander .................... 433/29 |
| 2003/0156788 A1 * | 8/2003 | Henning ...................... 385/31 |
| 2004/0254478 A1 * | 12/2004 | de Josselin de Jong et al. .. 600/476 |
| 2005/0202372 A1 * | 9/2005 | Rapczynski ................. 433/215 |

FOREIGN PATENT DOCUMENTS

DE    196 19 067 A1    11/1997

* cited by examiner

*Primary Examiner*—John J Wilson
(74) *Attorney, Agent, or Firm*—Gerald E. Hespos; Anthony J. Casella

(57) ABSTRACT

A tooth is irradiated with light (5), in particular with visible light for identifying tooth-colored tooth filling residues (3) of the tooth. The light with which the irradiation procedure is effected includes at least one wavelength component that is absorbed or scattered by the tooth filling material differently from the tooth material in such a way that the tooth filling material differs from the tooth material in respect of its brightness or in respect of its color. Thus the identification of tooth filling residues (3) can be effected in such a way that the dentist can recognise the tooth filling residues (3) with the naked eye, or possibly with the assistance of simple technical aids such as for example a color filter.

13 Claims, 8 Drawing Sheets

METHOD FOR IDENTIFYING TOOTH-COLORED TOOTH FILLING RESIDUES

BACKGROUND OF THE INVENTION

1. Field of the Invention

The invention concerns a method and apparatus for identifying tooth-coloured tooth filling residues.

2. Description of the Related Art

For some time now tooth fillings have been used in dental medicine, which can no longer be readily distinguished from healthy tooth. If those fillings have to be removed it is difficult for the dentist to see whether the filling has been completely removed.

Therefore technical aids have been proposed for discovering tooth filling residues. DE 196 19 067 proposes distinguishing tooth filling residues from the tooth-substance on the basis of the differing scatter characteristics thereof in relation to Raman scattering. To find tooth filling residues, the free end of an optical fibre, at the other end of which there is a laser, is directed on to the tooth. Light scattered by the tooth substance is collected by means of a collector device and fed to an evaluation unit where it is spectrally filtered or split up. Detection of the tooth filling material is then effected in the evaluation unit on the basis of characteristic intensities. The result of the detection procedure is communicated to the dentist by way of a display device or automatically registered by means of a registration device. However such an apparatus requires relatively complicated and expensive analysis of the scattered light as well as a relatively high level of technical expenditure for displaying the result of the analysis procedure.

Therefore the object of the present invention is to provide a method of identifying tooth filling residues, by means of which the detection of tooth-coloured tooth filling residues can be simplified. A further object of the invention is to provide an apparatus for carrying out the method.

SUMMARY OF THE INVENTION

In the method of the invention for identifying tooth-coloured tooth filling residues of a tooth, the tooth is irradiated with light, in particular visible light. In that connection, the light with which the irradiation operation is effected includes at least one wavelength component which is absorbed or scattered by the tooth filling material differently from the tooth material such that the tooth filling residue differs from the tooth material in its brightness, that is to say in the intensity of the scattered light, or in its colour. In that respect the term wavelength component denotes an individual wavelength or a wavelength range and the term colour difference denotes a spectral difference between the light scattered by the tooth material and the light which is scattered by the tooth filling material and which makes itself noticeable in the visible wavelength range.

By virtue of the differing absorption or scatter of at least one wavelength component, the tooth filling material can be distinguished from the tooth material on the basis of differences in brightness or colour in comparison with the tooth material. Therefore the method according to the invention makes it possible to implement identification of tooth filling residues in such a way that, with the naked eye, possibly with the assistance of simple technical aids, such as for example a colour filter, the dentist can recognise the tooth filling residues. There is no need for the light scattered by the tooth to be spectrally analysed or spectrally split up, to recognise the tooth filling residues, just as there is no need for a display device for displaying the result of the analysis procedure. The technical expenditure which has to be incurred in order to recognise tooth-coloured tooth filling residues is therefore lower than in the state of the art.

In a first variant of the method according to the invention irradiation of the tooth is effected in a locally limited region which can be given for example by a point or a line. In that case the irradiation operation can be effected both with coherent and also with incoherent light. If the point or the line of the light used for the irradiation operation is of a very small extent, the method can include a step of scanning the region of the tooth in which the tooth filling residues are present. In that respect irradiation in line form affords the advantage that scanning needs to be effected only in one direction.

The first variant makes use of the fact that visible light is greatly scattered in the tooth material, in particular in the dentine, but is absorbed only to a slight degree. In contrast, in most cases the light is absorbed by the tooth filling material to a greater degree than by the tooth material. Upon local irradiation of the tooth the scattered light issues from the tooth again in the region around the illumination point so that a bright halo effect appears around the illumination point. As a filling residue generally absorbs more light than the tooth material, the filling residues in the region of the halo effect generally appear darker than the tooth material or even quite black. Therefore tooth filling materials can be easily recognised with the naked eye, possibly with the aid of a colour filter. It should be noted however that the scattering characteristics of teeth and filling material can differ greatly from one person to another or from one filling material to another. It can therefore also happen that the filling residues absorb less light than the tooth material. In those cases the method provides a result in which the tooth filling residues appear correspondingly brighter in the halo area than the tooth material.

If the irradiation operation is effected with coloured, in particular monochromatic, light, the wavelength of the light can be adapted to the tooth filling material or the sensitivity of the eye in such a way that the difference in brightness between the tooth material and the tooth filling material to be identified or perception of the difference is optimised. It is particularly advantageous if the procedure uses that wavelength in which the difference in the absorption and/or scattering characteristics between the tooth material and the tooth filling material is at its greatest, as then the levels of intensity of the scattered light from the materials differ greatly. In particular red or green light has proven to be highly suitable.

In a second variant of the method according to the invention the irradiation operation is effected with light, the spectrum of which has irregularly distributed wavelengths. That variant is based on the realisation that visible light is generally scattered greatly with a very low level of dependency on wavelength by the tooth material, in particular the dentine, but is absorbed only to a slight degree. In contrast, depending on the material involved, wavelength-dependent scattering and absorption occurs in tooth fillings. If the tooth is irradiated with light which has a spectrally irregular wavelength distribution, it is possible to recognise colour differences and/or differences in intensity between the tooth material which scatters the light independently of wavelength and the tooth filling material which scatters the light in dependence on wavelength, using the naked eye or with the aid of a filter. In particular the irregularly distributed wavelengths can be afforded by at least two wavelengths in respect of which the absorption and/or scattering capability of the tooth material differs greatly from that of the tooth filling material.

The wavelength distributions can also be so selected that the tooth filling material or the tooth material, in respect of at least one of those wavelengths, exhibits an extreme, that is to say a maximum or a minimum, in terms of scattering and/or absorption characteristics. In that respect the maximum or minimum does not necessarily need to be an absolute maximum or minimum (maximum with the highest scattering or absorption capability of all maxima or minimum with the lowest scattering or absorption capability of all minima), but rather it is also possible to use local maxima or minima (that is to say, maxima or minima whose scattering or absorption capability does not correspond to that of the greatest maximum or minimum respectively), and that increases the number of wavelengths which can be used. In that respect, in particular also economic aspects may be significant in terms of the choice of the wavelengths used. Thus light sources for different wavelengths involve for example different costs. Therefore, when choosing the wavelengths, it is possible to weigh up between suitability for use in the method and the economy aspect, for example a maximum with a scattering or absorption capability which is not quite so high can be selected if the corresponding light source is markedly cheaper than that for the wavelength of a different maximum.

In a configuration of the second variant the distribution of the wavelengths is so selected that the blend of the wavelengths appears white. That can be embodied in particular by the spectrum having three wavelengths, for example red, green and blue, the blend of which gives white light. In that case tooth material as a wavelength-independent scattering material appears white. In contrast tooth filling residues, as generally wavelength-dependent scattering material, exhibit a colour tint, on the basis of which they can be identified.

In an alternative configuration of the second variant wavelength distribution in the spectrum is so selected that the spectrum exhibits a given colour temperature. Usually the colour shade of the tooth filling material is adapted to the colour shade of the tooth in such a way that the tooth filling material is not to be distinguished from the healthy tooth either in daylight or with ambient illumination. If however the colour temperature is changed, differences between healthy tooth and tooth filling residues can be detected.

The light with which the irradiation operation is effected in the method according to the invention can exhibit for example a Gaussian profile in respect of its irradiation cross-section. Under some circumstances however that can mean that it is only with difficulty that it is possible to see whether differences in intensity which occur in the scattered light are to be attributed to variations in intensity in the Gaussian profile of the irradiation light or whether they are due to the difference in the scattering or absorption characteristics of tooth material and tooth filling material. In an advantageous development of the method according to the invention therefore the irradiation operation can be effected with light in respect of which the distribution of intensity in the irradiation cross-section has a constant portion in at least one direction. In particular the irradiation procedure can be effected with a light beam whose intensity distribution in the radial direction has a constant portion, for example in the form of a so-called hat top pattern. With that configuration, the above-indicated problems do not occur or occur only to a slight degree as the irradiated regions are irradiated substantially with light of the same intensity.

Besides the method of identifying tooth-coloured tooth filling residues the invention also provides an apparatus for carrying out the method.

An apparatus according to the invention for identifying tooth-coloured tooth filling residues of a tooth includes an irradiation device for irradiating the tooth with light. The irradiation device includes a light source which is distinguished in that it radiates light with at least one wavelength component which is absorbed or scattered by the tooth filling material differently from the tooth material in such a way that the tooth filling residue differs in respect of its brightness or its colour from the tooth material. In addition there may be an adjusting device for adjusting or attenuating the intensity of the light from the light source and the irradiation device can be designed in particular for example in such a way that it illuminates the tooth in the form of a point or a line.

In a first configuration of the apparatus the irradiation device is such that it permits local irradiation of the tooth. In addition the light source radiates light with at least one wavelength component which is absorbed or scattered by the tooth filling material differently from the tooth material in such a way that the tooth filling residue differs from the tooth material in respect of its brightness.

The irradiation device can be in particular in the form of a pen which includes the light source and which is so designed that it is to be held directly against the tooth.

Alternatively the irradiation device may also include a light guide or optical fibre which is connected to the light source and which in particular can be of such a nature that it is to be held directly against the tooth. An optical means can optionally be arranged at the distal end of the light guide. In that way the light source itself can be stationary, so that less severe limits are imposed on the design configuration of the light source, than if it is to be integrated into a pen.

In a further configuration the irradiation device can be integrated into an operating microscope for observing the tooth. In particular it can be so designed that the illumination point is displaced relative to the focal point of the operating microscope. Observation of the tooth is facilitated by virtue of the fact that observation takes place in a region in which the halo is not outshone by light from the irradiation device, which is reflected by the surface of the tooth. Alternatively, that can also be achieved by the irradiation device being so designed that illumination takes place in an annular configuration around the focal point of the operating microscope.

Suitable light sources are lasers and diode lasers but also incoherent light sources such as for example LEDs.

In a second configuration of the apparatus according to the invention the light source is such that the spectrum thereof exhibits an irregular wavelength distribution, in which respect the blend of wavelengths can give in particular white light. The spectrum includes at least one wavelength component which is absorbed or scattered by the tooth filling material differently from the tooth material in such a way that the tooth filling material differs from the tooth material in respect of its colour. The irradiation device can include in particular three monochromatic light sources, the radiations of which exhibit different wavelengths.

In a third configuration of the apparatus according to the invention associated with the light source is an adjusting device for adjusting the colour temperature of the light emanating from the light source. The adjusting device can be used to adjust the colour temperature of the light in such a way that differences between healthy tooth and tooth filling residues are clearly apparent.

In the apparatus according to the invention the light with which the irradiation operation is effected can involve, in at least one direction, a profile with a constant intensity distribution. If the irradiation device is so designed that it illuminates the tooth in point form, the point can have in particular an intensity distribution which has a constant portion in the radial direction. As stated above, a profile with an intensity distribution which has a constant portion, for example a hat top profile, can have the advantage over a Gaussian profile that fewer fluctuations in intensity occur in the irradiated region of the tooth.

In addition the irradiation device of the apparatus according to the invention can be integrated into an operating microscope or an OP-illumination means. It will be appreciated that it can also be in the form of an independent unit. Furthermore the apparatus according to the invention can include a scanning unit for scanning the tooth. Finally it may also have an adjusting device for adjusting the level of intensity of the light used for the irradiation procedure in order to give the user the option of adjusting an intensity which makes it easier for him to detect the tooth filling residues and which is pleasant for him.

Further features, properties and advantages of the invention are described hereinafter by means of embodiments with reference to the accompanying Figures.

DETAILED DESCRIPTION OF THE PREFERRED EMBODIMENTS

A first embodiment of the method according to the invention is described hereinafter with reference to FIG. 1.

Figure 1:
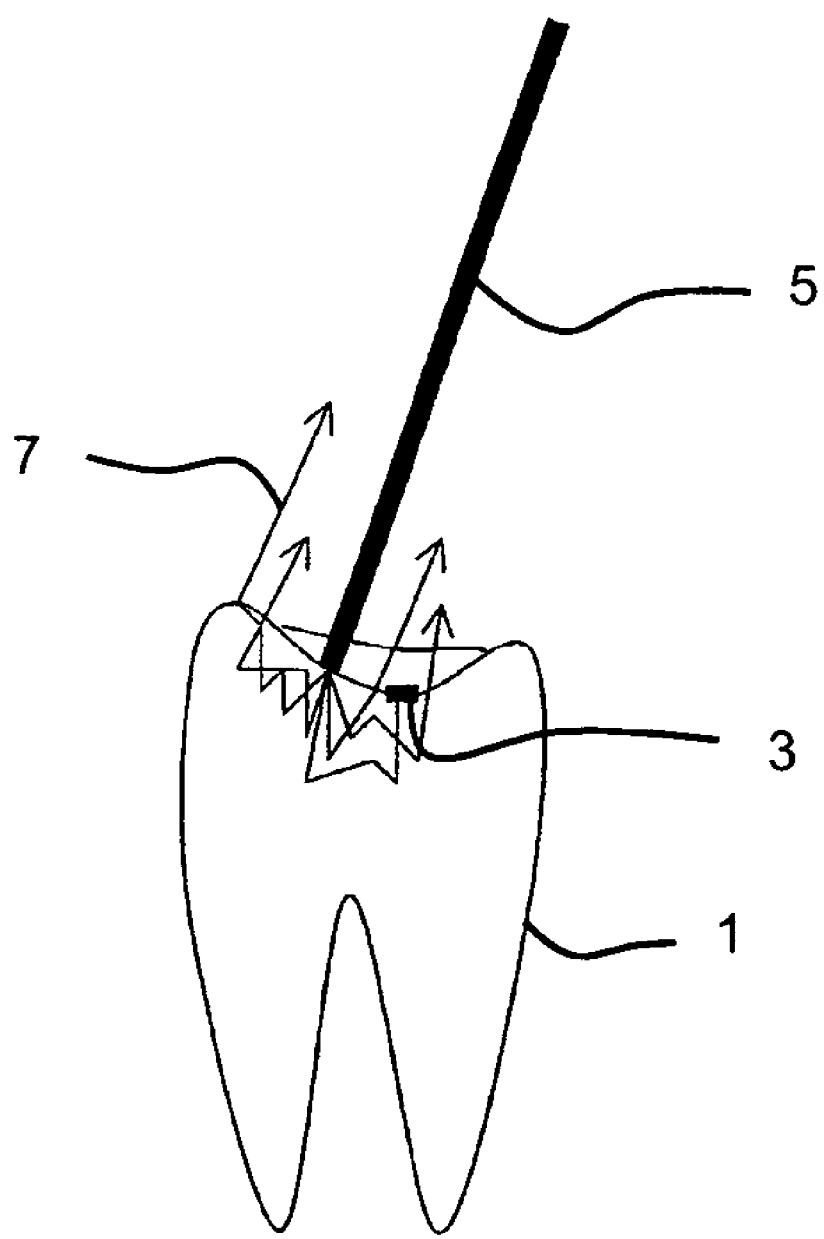
FIG. 1 shows a first embodiment of the method according to the invention.
Figure 8:
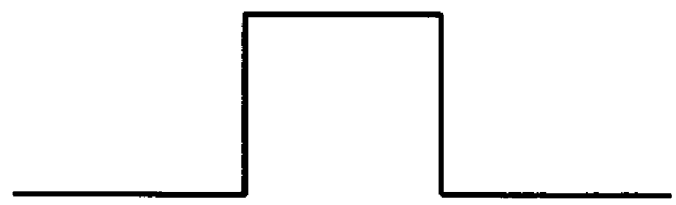
FIG. 8 shows a possible intensity profile of a light beam used in the invention in the radial direction.

Referring to FIG. 1 illustrated therein are a tooth 1, a tooth filling residue 3 and a light beam 5 with which the tooth 1 is irradiated in a locally limited region. In the radial direction the light beam 5 involves the hat top profile illustrated in FIG. 8 as its intensity profile and is preferably formed from coloured and in particular monochromatic light. The wavelength or wavelengths of the light beam 5 is or are so selected that the light is strongly scattered by the tooth material, in particular the dentine, but is greatly absorbed by the tooth filling material. In the present embodiment red or green light is used. The light scattered by the tooth material then issues inter alia around the irradiated region, as is indicated by the arrows 7 in FIG. 1. Therefore a coloured halo appears around the illumination point. The scattered light is however absorbed by the tooth filling material more greatly than by the tooth material so that less scattered light issues from the tooth at the location of the tooth filling residue 3, whereby the tooth filling residue 3 appears darker than the tooth material surrounding it. In the extreme case the tooth filling residue 3 can even appear entirely black.

It has been assumed in the described embodiment that the tooth filling material 3 absorbs the light used for irradiation purposes more greatly than the tooth material 1. It should be pointed out however that this is not a prerequisite for proper operation of the method according to the invention. The only important consideration is that the absorption and/or scattering characteristics of tooth filling material 3 and tooth material 1 differ for the light selected for the irradiation procedure and that this difference is perceptible in terms of a difference in brightness or colour in the light scattered by the tooth filling material 3 and the tooth material 1 respectively. For example, depending on the material used and the individual absorption characteristics of the teeth, the tooth filling material 3 can also absorb the light selected for the irradiation procedure to a lesser degree than the tooth material. In that case the tooth filling material 3 would appear brighter than the tooth material 1. A corresponding consideration also applies in regard to the embodiments described hereinafter.

Figure 9:
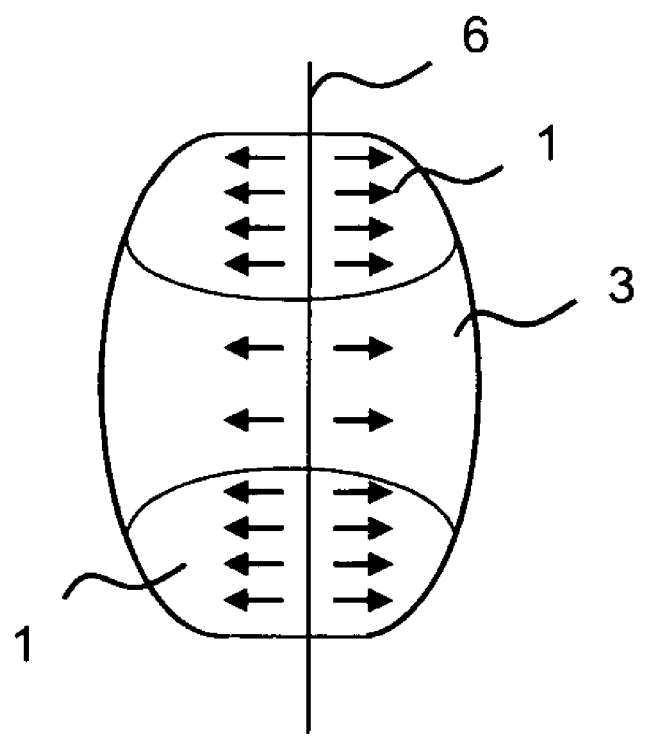
FIG. 9 shows an alternative configuration of the embodiment shown in FIG. 1.

In an alternative configuration of the first embodiment irradiation of the tooth 1 is not effected in the form of a point but in the form of a line as is shown in FIG. 9. The intensity profile of the light, perpendicularly to the direction in which it extends, preferably has a constant portion, for example in the form of a very narrow hat top profile. In the regions on both sides of the irradiation line 6, it is possible to distinguish between the tooth material 1 and the tooth filling material 3, on the basis of the intensity of the scattered light. By virtue of the greater absorption of the light in the tooth filling material 3 the regions on both sides of the irradiation line 6, where the tooth material 1 is disposed, appear brighter than where the tooth filling material 3 is to be found. The dentist can ascertain the extent of the tooth filling or tooth filling residues by scanning the tooth 1 perpendicularly to the direction in which the irradiation line 6 extends.

Figure 2:
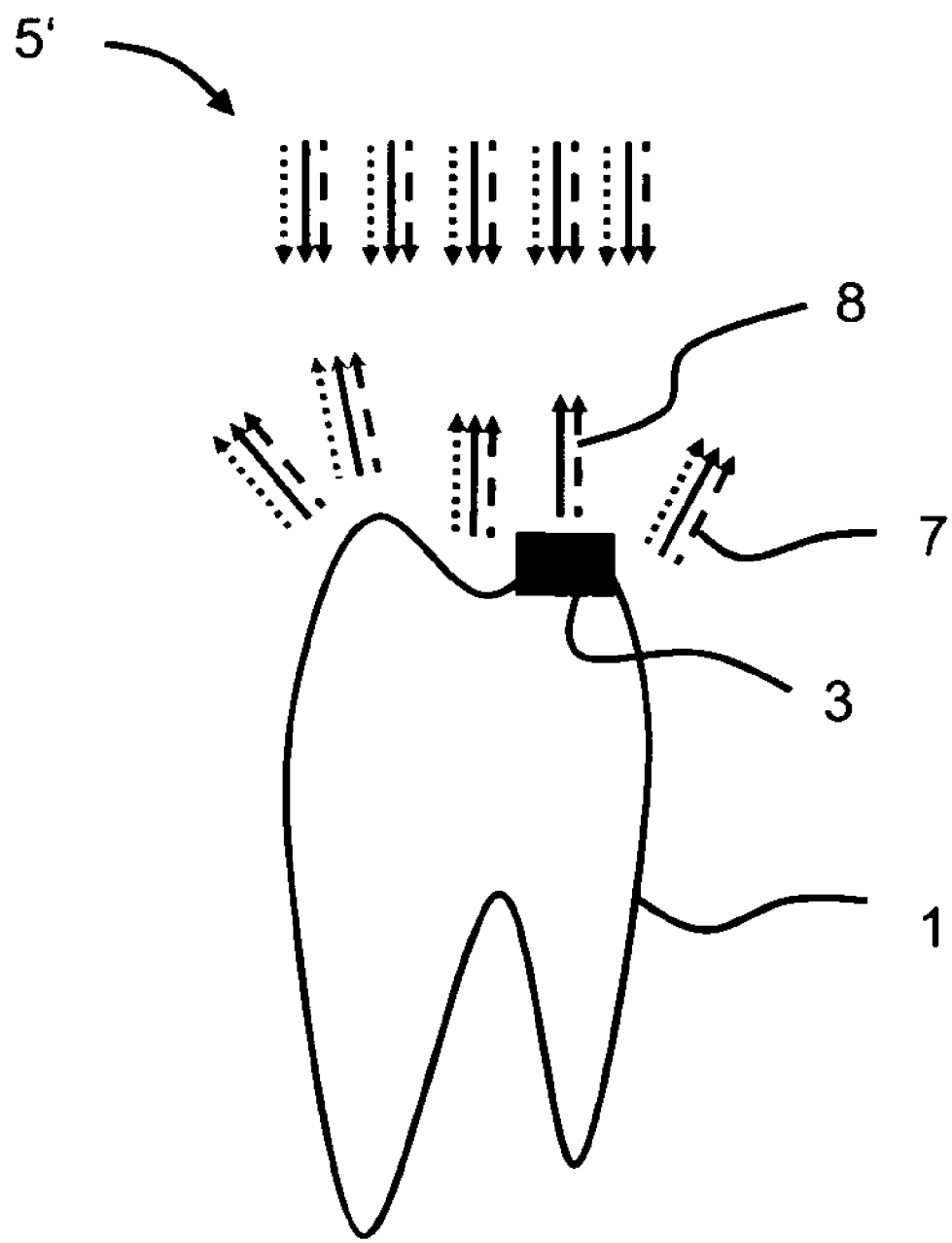
FIG. 2 shows a second embodiment of the method according to the invention.

FIG. 2 shows a second embodiment of the method according to the invention. In this embodiment the tooth is irradiated with light 5' over a large area. The light used for the irradiation procedure involves a spectrum with irregularly distributed wavelengths and is preferably of an intensity which is substantially constant over the entire irradiation cross-section. It appears white however in the blend of the wavelengths. In the illustrated embodiment the spectrum includes red, green and blue light, as is indicated in FIG. 2 by dotted, solid and broken lines respectively. The light 5' is scattered by the tooth material and a part of the scattered light 7 issues from the tooth 1 again. As the tooth material, in particular the dentine, scatters visible light only with a very low level of wavelength dependency, the scattered light 7 appears substantially white like the light 5' with which the tooth 1 is irradiated.

In contrast to the tooth material however the tooth filling material involves wavelength-dependent scattering and absorption characteristics. In the region of a tooth filling residue 3 therefore the scattered light involves a coloured tint, on the basis of which the tooth filling residue 3 can be easily identified.

The wavelengths of the spectrum of the light used for the irradiation procedure are preferably so selected that they are scattered to greatly different degrees by the tooth filling material.

Admittedly, the present embodiment uses a mixture of red, green and blue light for irradiating the tooth, but it is sufficient if at least two different wavelengths are used. Admittedly, the tooth then no longer appears white but it is still possible to establish a colour difference between the tooth material and the tooth filling material, in particular when the wavelengths used are adapted to the scattering or absorption capability of the tooth material and/or the tooth filling material.

In a modification of the second embodiment irradiation of the tooth 1 can also be effected with light whose colour temperature is variable.

Usually the colour shade of the tooth filling material is matched to the tooth in such a way that the tooth filling cannot be distinguished from the tooth material either in daylight or under ambient lighting. On the basis of a variation in the colour temperature, for example of light whose colour temperature corresponds to daylight, in relation to light whose colour temperature corresponds to ambient lighting, it is possible to detect differences between tooth material and tooth filling material, which are due to the wavelength-dependent scattering and absorption characteristics of the tooth filling material. If the scattering and absorption characteristics of the tooth filling material are already known in advance, the colour temperature of the light used for the irradiation procedure can be adapted from the outset to the tooth filling material in such a way that the differences which occur between the tooth material and the tooth filling material are easy to recognise.

FIGS. 3 to 7 show various embodiments of the apparatus according to the invention for identifying tooth-coloured tooth filling residues of a tooth.

Figure 3:
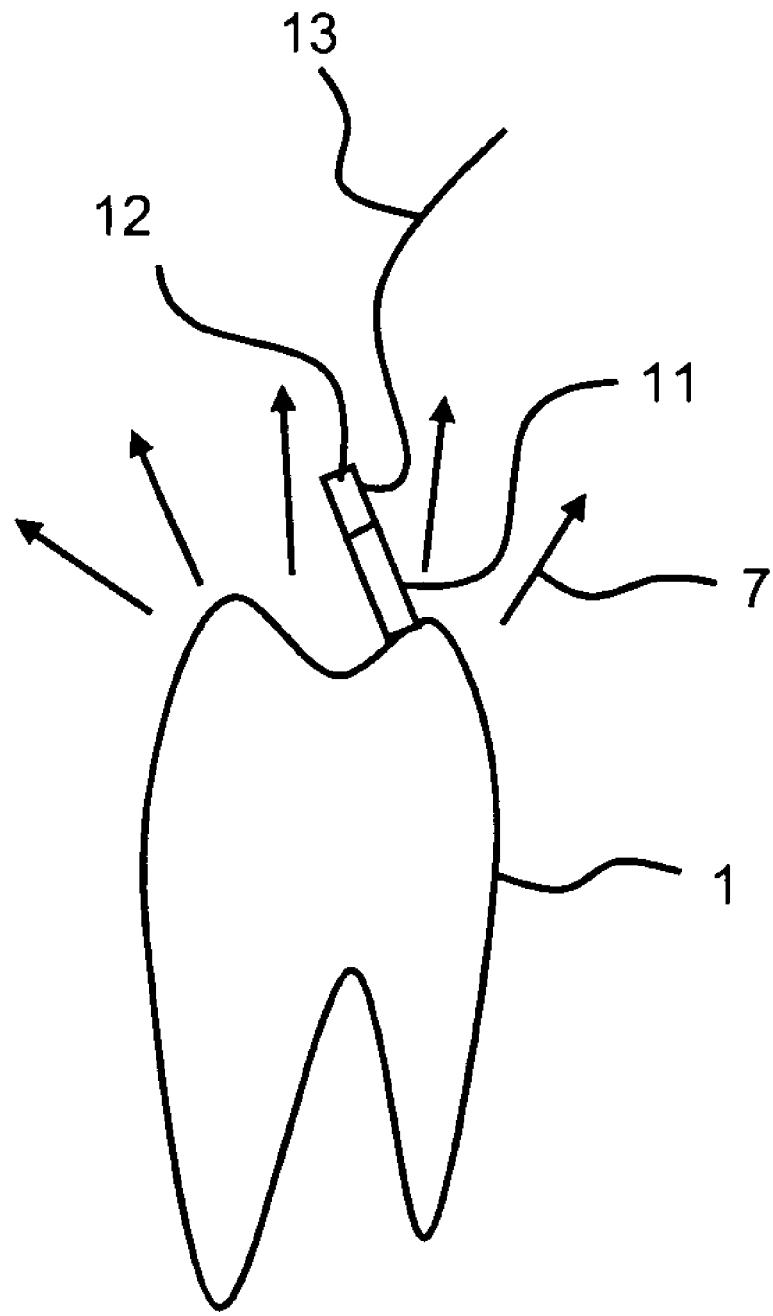
FIG. 3 shows a first embodiment of the apparatus according to the invention for identifying tooth-coloured tooth filling residues of a tooth.

FIG. 3 shows a first embodiment of the apparatus according to the invention. This embodiment is suitable for carrying out the method in accordance with the first embodiment of the method of the invention.

The Figure shows the tooth 1 and the scattered light 7. For local irradiation of the tooth 1 the apparatus has an irradiation device which is in the form of a pen 11. To adjust the intensity of radiation the irradiation device also has an intensity regulator (not shown).

The pen 11 includes a light source 12 which produces for example red or green light and can be held directly against the tooth 1 for local irradiation thereof. It produces a light point, the radial intensity distribution of which corresponds to the hat top profile shown in FIG. 8. The light source 12 is supplied with power by way of a line 13 but alternatively it can also be supplied with power by means of an energy storage means integrated into the pen 11, such as for example a battery or an accumulator.

Coherent light sources such as for example lasers or diode lasers but also incoherent light sources such as for example LEDs can be used as the light sources 12.

Figure 4:
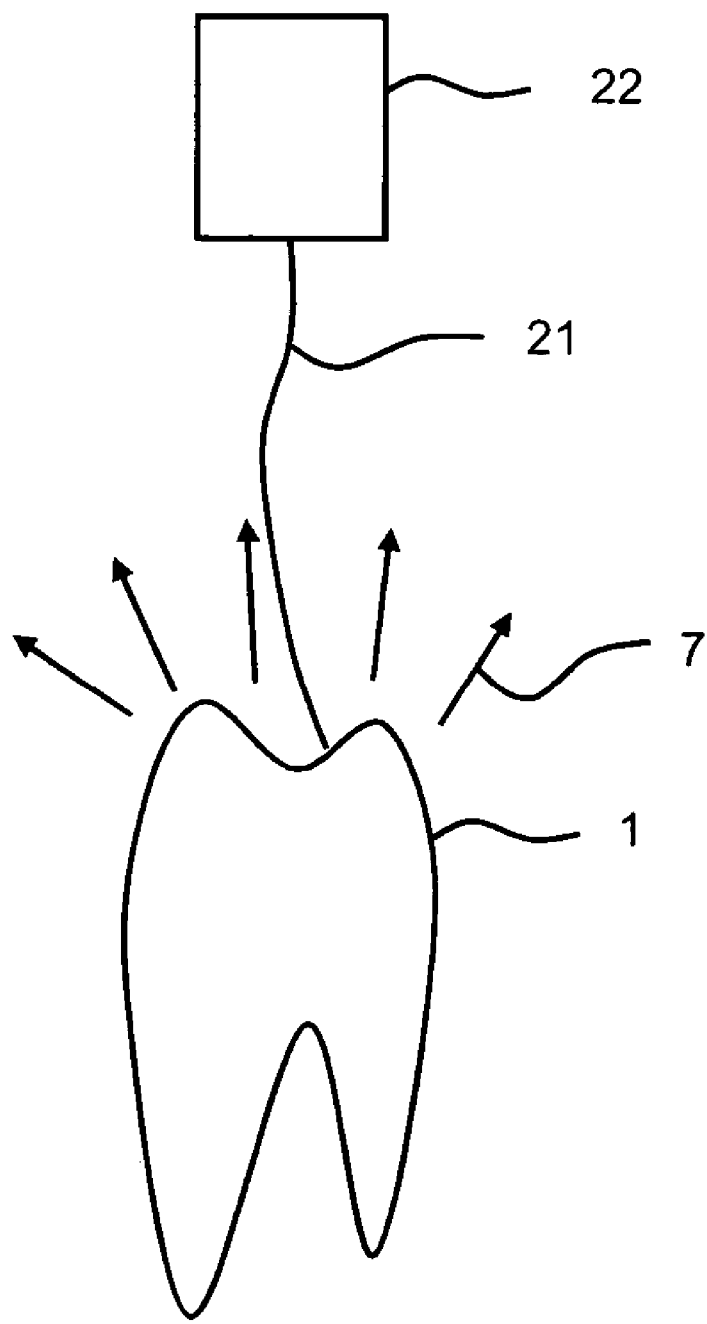
FIG. 4 shows a second embodiment of the apparatus according to the invention for identifying tooth-coloured tooth filling residues of a tooth.

FIG. 4 shows a second embodiment of the apparatus according to the invention. This embodiment is also suitable for carrying out the method in accordance with the first embodiment of the method of the invention.

The embodiment shown in FIG. 4 differs from the embodiment illustrated in FIG. 3 in that the irradiation device, instead of a pen 11 with an integrated light source 12, includes a stationary light source 22 and a light guide or optical fibre 21. The light guide 21 can be held against the tooth so that the tooth can be irradiated locally with the light of the light source 22 by means of the light guide 11.

Figure 5:
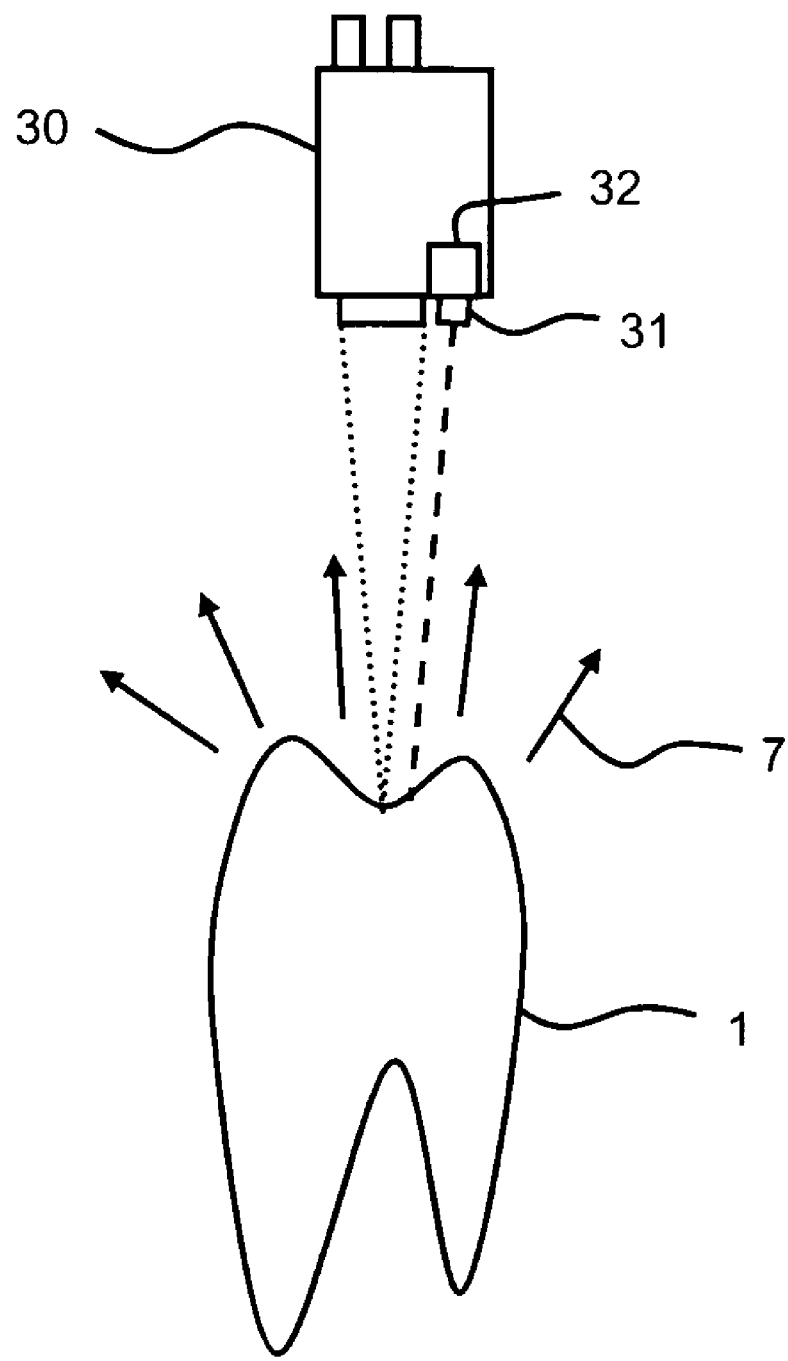
FIG. 5 shows a third embodiment of the apparatus according to the invention for identifying tooth-coloured tooth filling residues of a tooth.

FIG. 5 shows a third embodiment of the apparatus according to the invention. This embodiment is also suitable for carrying out the method in accordance with the first embodiment of the method of the invention.

Besides the tooth 1 and the scattered light 7 the Figure also shows an operating microscope 30, into which an irradiation unit 31 and 32 is integrated. The irradiation unit includes a light source 32 which produces for example red or green light as well as an optical focusing means 31, by way of which irradiation of the tooth 1 can be locally limited. The optical focusing means 31 can be of such a configuration that the light from the light source 32 is focused on to a point which is slightly displaced relative to the focal point of the microscope 30. In the simplest case a single focusing lens can then serve as the optical focusing means 31. Alternatively the optical focusing means 31 can also be designed in such a way that irradiation of the tooth 1 is effected in an annular configuration around the focal point of the microscope 30. Fluctuations in brightness in the coloured halo, which are not to be attributed to tooth filling residues, are reduced by the annular illumination effect. As a further alternative irradiation can be effected in the form of a line, as is illustrated in FIG. 9. In that case the irradiation device additionally includes a scanning device in order to be able to scan the tooth with the line. A scanning device can however also be provided when illumination in point form or circle form is involved, in particular if the point or circle cross-section is very small or the region of the tooth to be investigated is large.

Examination of the tooth 1 for tooth filling residues is effected with the operating microscope 30. It will be appreciated that the examination procedure can also be effected by means of an operating microscope when the irradiation unit is not integrated into the operating microscope but is in the form of an independent unit.

Figure 6:
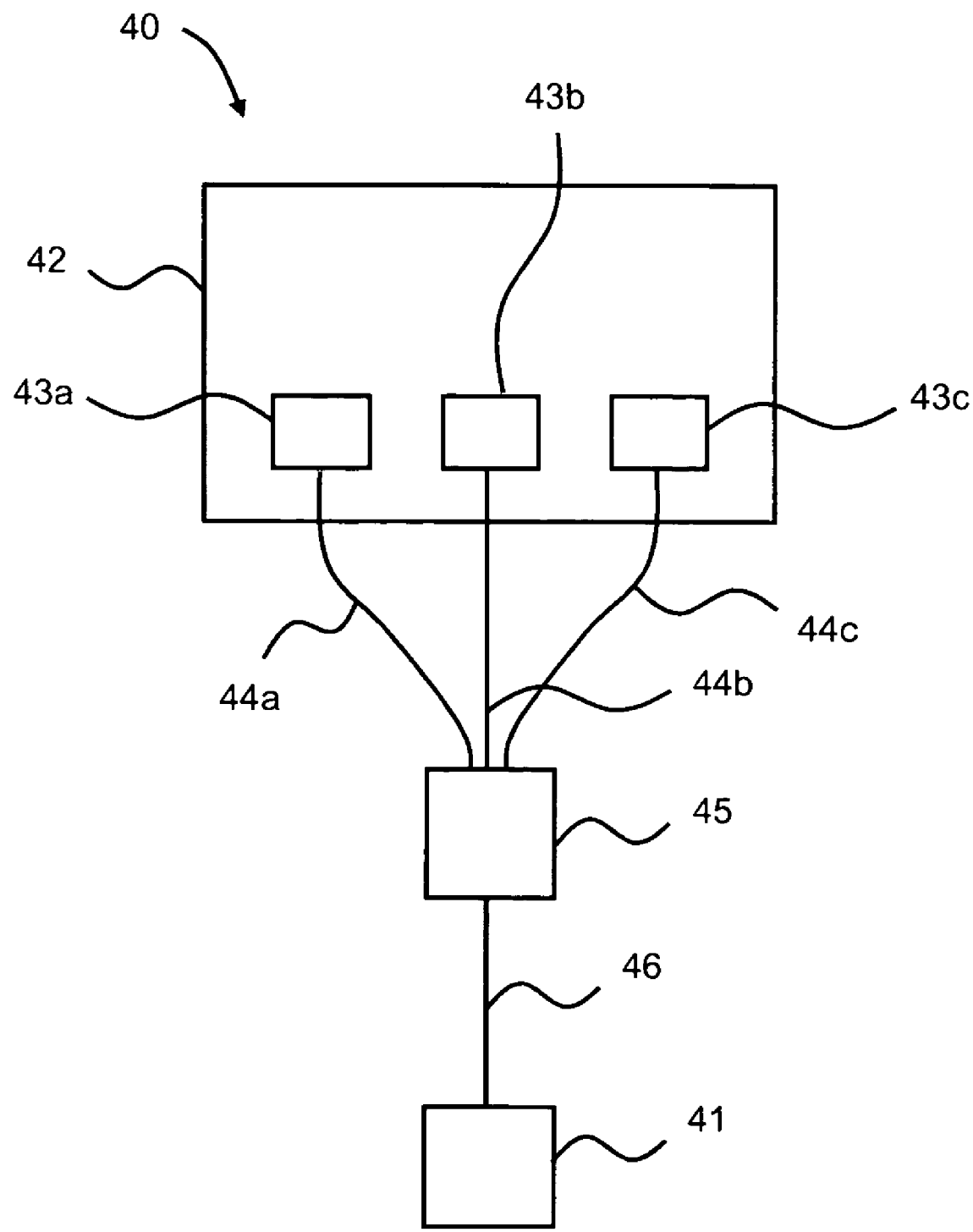
FIG. 6 shows a fourth embodiment of the apparatus according to the invention for identifying tooth-coloured tooth filling residues of a tooth.

FIG. 6 shows a fourth embodiment of the apparatus according to the invention. This embodiment is designed for carrying out the method in accordance with the second embodiment of the method of the invention.

Illustrated here is an irradiation apparatus 40 which includes a light source unit 42 for producing white light and an optical irradiation means 41 for irradiating the tooth with the white light. The light source unit includes three light sources 43a, 43b, 43c for producing red, green and blue light. For example lasers or LEDs can be used as the light sources 43a, 43b, 43c. The light sources 43a, 43b, 43c are connected by way of light guides 44a, 44b, 44c to a mixer 45 in which the light is mixed in such a way that the mixed light appears white. The mixer 45 is connected to an optical irradiation means 41 by way of a further light guide 46. The optical irradiation means 41 is of such a configuration that the tooth can be irradiated with the mixed light, in particular over a large area and uniformly. In order to ensure uniform irradiation the optical irradiation means 41 is for example of such a design configuration that the beam cross-section in the radial direction involves the hat top profile shown in FIG. 8.

Figure 7:
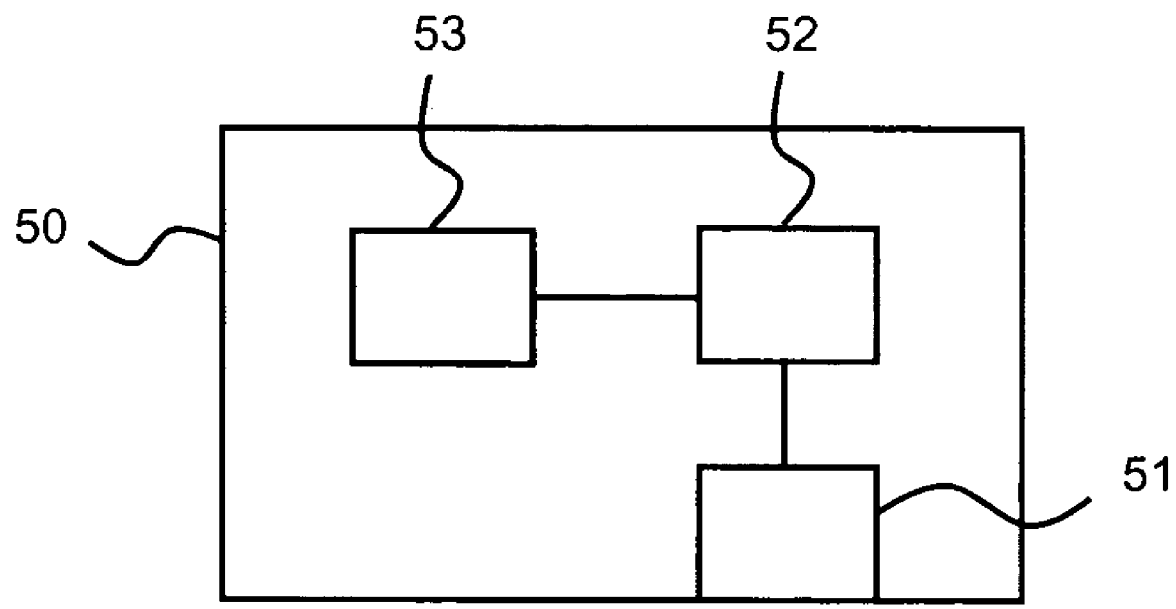
FIG. 7 shows a fifth embodiment of the apparatus according to the invention for identifying tooth-coloured tooth filling residues of a tooth.

A fifth embodiment of the apparatus according to the invention is shown in FIG. 7. The apparatus 50 includes a light source 52 and an optical irradiation means 51, by means of which the tooth can be irradiated with the light from the light source in particular over a large area and uniformly. It is also advantageous in this embodiment if the beam cross-section involves a constant intensity distribution.

The light source 52 is of such a nature that its colour temperature can be varied by means of an adjusting device 53 connected to the light source. For the purposes of identifying tooth filling residues, the colour temperature can be varied by means of the adjusting device until a colour temperature is set, at which the tooth filling material differs from the tooth material. If the scattering or absorption characteristics of the tooth filling material are known, the colour temperature can also be already set prior to the irradiation procedure, in such a way that the tooth filling material can be recognised. In that case there is no need to search for the correct adjustment.

All the described embodiments can have an adjustment option for adjusting the intensity of the light used for the irradiation procedure in order to give the user the option of adjusting the intensity to a value which is pleasant for him and which guarantees an optimum distinction between tooth material and tooth filling material.

What is claimed is:

1. A method of identifying tooth-coloured tooth filling residues of a tooth, in which the tooth is irradiated with light, characterised in that the irradiation operation is effected with light whose spectrum has irregularly distributed wavelengths which includes at least one wavelength component which is absorbed or scattered by the tooth filling material differently from the tooth material in such a way that the tooth filling residue differs from the tooth material in respect of its brightness or in respect of its colour, wherein the distribution of the wavelengths in the spectrum is so selected that the spectrum has substantially a given colour temperature, the given colour temperature being selected to visually distinguish the tooth filling material with the naked eye.

2. The method according to claim 1 wherein irradiation of the tooth is effected in a locally limited region.

3. The method according to claim 2 wherein the locally limited region represents a line.

4. The method according to claim 2 wherein a scanning of the tooth is effected with the irradiation light.

5. The method according to claim 1 wherein the irradiation procedure is effected with light which is of a wavelength at which the difference in the absorption and/or scattering characteristics of tooth material and tooth filling material is at its greatest.

6. The method according to claim 1 wherein the irradiation operation is effected with coloured, in particular monochromatic light.

7. The method according to claim 6 wherein the irradiation operation is effected with red or green light.

8. The method according to claim 1 wherein the spectrum has at least two wavelengths, in respect of which the absorption and/or scattering capability of the tooth material differs greatly from that of the tooth filling material.

9. The method according to claim 1 wherein the wavelengths are so selected that the tooth filling material or the tooth material has in respect of at least one of said wavelengths an extreme in scattering and/or absorption characteristics.

10. The method as set forth in claim 1 wherein the distribution of the wavelengths in the spectrum is so selected that the mixture of the wavelengths gives white light.

11. The method according to claim 10 wherein the spectrum has three different wavelengths, the mixture of which gives white light.

12. The method according to claim 1 wherein the irradiation step is effected with light whose intensity distribution has a constant portion in at least one direction.

13. The method according to claim 12 wherein the irradiation step is effected with a light beam whose intensity distribution has a constant portion in the radial direction.

* * * * *